United States Patent [19]

Kapa et al.

[11] Patent Number: 4,847,384

[45] Date of Patent: Jul. 11, 1989

[54] PROCESS FOR THE PREPARATION OF CERTAIN NITROGEN-CONTAINING MONO- AND BICYCLIC ACE INHIBITORS, AND NOVEL INTERMEDIATES USEFUL THEREFOR

[75] Inventors: Prasad K. Kapa, Parsippany; Kau-Ming Chen, Randolph, both of N.J.

[73] Assignee: Sandoz Pharm. Corp., E. Hanover, N.J.

[21] Appl. No.: 24,959

[22] Filed: Mar. 12, 1987

[51] Int. Cl.$^4$ .................. C07D 207/16; C07D 209/96
[52] U.S. Cl. ..................................... 548/409; 548/158; 548/533
[58] Field of Search ............... 558/250, 256; 548/158, 548/533, 409

[56] References Cited

U.S. PATENT DOCUMENTS

| | | | |
|---|---|---|---|
| 1,958,770 | 5/1934 | Sebrell | 548/158 |
| 4,325,945 | 4/1982 | Natarajan et al. | 548/409 X |
| 4,506,082 | 3/1985 | Crossley | 548/533 |
| 4,512,979 | 4/1985 | Patchett et al. | 548/533 X |

*Primary Examiner*—Joseph Paul Brust
*Attorney, Agent, or Firm*—Gerald D. Sharkin; Robert S. Honor; Joseph J. Borovian

[57] ABSTRACT

An improved process for preparing certain nitrogen-containing mono- and bicyclic ACE inhibitors comprising reacting an α-alkyl amino acid with a disulfide compound to form a thioester intermediate, which intermediate is then amidated with a mono- or bicyclic amino acid. The invention also relates to the novel thioester intermediates prepared by the first step of the process.

20 Claims, No Drawings

PROCESS FOR THE PREPARATION OF CERTAIN NITROGEN-CONTAINING MONO- AND BICYCLIC ACE INHIBITORS, AND NOVEL INTERMEDIATES USEFUL THEREFOR

The present invention relates to an improved process for preparing certain nitrogen-containing mono- and bicyclic ACE inhibitors comprising reacting an α-alkyl amino acid with a disulfide compound to form a thioester intermediate, which intermediate is then amidated with a mono- or bicyclic amino acid.

Suitable ACE inhibitors which may be prepared by the process of this invention include the monocyclic compounds having the formula

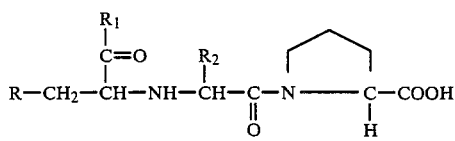

wherein
R is $C_1$–$C_6$ alkyl, benzyl, benzylthio, benzyloxy, phenylthio or phenoxy;
$R_1$ is hydroxy or $C_1$–$C_6$ alkoxy;
and $R_2$ is hydrogen, $C_1$–$C_6$ alkyl or $C_1$–$C_6$ aminoalkyl.

In the above formula, preferred compounds are those wherein R is benzyl, $R_1$ is $C_1$–$C_6$ alkoxy and $R_2$ is hydrogen, methyl or aminobutyl. More preferred compounds of the above formula are those wherein R is benzyl, $R_1$ is $C_1$–$C_4$ alkoxy and $R_2$ is hydrogen or methyl. The even more preferred compounds of the above formula are those wherein R is benzyl, $R_1$ is ethoxy and $R_2$ is methyl. The most preferred compound of the above formula is 1-[N-[1-(ethoxycarbonyl)-3-phenylpropyl]-L-alanyl]-L-proline having the formula

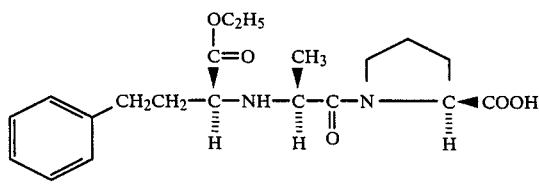

All of the above monocylic compounds are known, having been previously described in European Pat. No. 12,401. Moreover, their usefulness in treating hypertension as a result of their angiotensin converting enzyme (ACE) inhibitor properties, as well as methods for their preparation are set forth therein.

Other suitable ACE inhibitors which may be prepared by the process of this invention are the bicyclic compounds of the formula

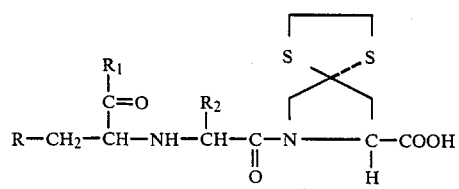

wherein R, $R_1$ and $R_2$ are as defined above.

The preferred, more preferred and even more preferred compounds of the above formula are as set forth above concerning the monocyclic compounds. The most preferred compound of the above formula is 7-[N-[1-(S)-ethoxycarbonyl-3-phenylpropyl]-(S)-alanyl]-1,4-dithia-7-azaspiro[4.4]nonane-8-(S)-carboxylic acid having the formula

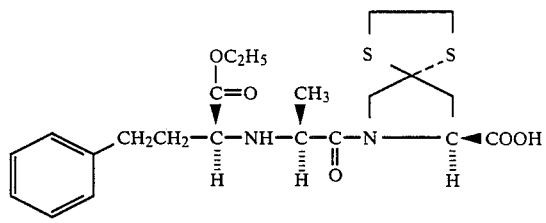

As with the above-depicted monocyclic compounds, all of the above bicyclic compounds are known, having been previously described in U.S. Pat. No. 4,470,972. Moreover, their usefulness in treating hypertension in view of their angiotensin converting enzyme inhibitor properties, as well as methods for their preparation, are set forth therein.

In contrast to the processes described in European Pat. No. 12,401 and U.S. Pat. No. 4,470,972 for preparing the pharmacologically active mono- and bicyclic compounds, respectively, the process of the present invention utilizes inexpensive raw materials and involves a simpler work-up as no solid by-products are formed.

In accordance with the process of the instant invention, the above-depicted mono- and bicyclic compounds are prepared by a two-step procedure involving, in a first-step, the reaction of an α-alkyl amino acid of formula I:

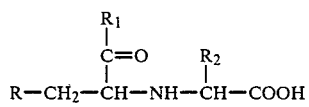

wherein
R, $R_1$ and $R_3$ are as defined above, with a disulfide compound of formula II.

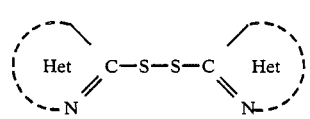

in which the two groups

are the same and signify a 5- or 6-membered heterocyclic ring, which ring may contain in addition to the nitrogen atom, one or two further hetero atoms selected from oxygen, nitrogen or sulfur, and which may be substituted or fused to a benzene ring which may itself be substituted, to obtain a thioester compound of formula III:

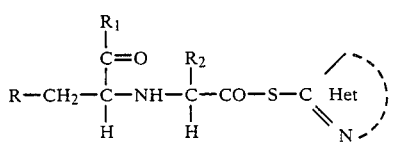

wherein R, $R_1$, $R_2$ and the group

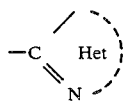

are as defined above.

In a second step, a thioester compound produced in the first step, i.e., a compound of formula III, is reacted with the monocyclic amino acid compound of formula IV:

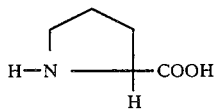

or the bicyclic amino acid compound of formula V:

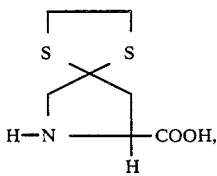

or an acid addition salt thereof, to produce the desired nitrogen-containing mono- or bicyclic compounds, respectively.

In the first step, an α-alkyl amino acid of formula I is reacted with a disulfide compound of formula II in the conjoint presence of a tri($C_1$-$C_4$) alkyl phoshine or phosphite, e.g. triethyl phosphite, or a triaryl phosphine or phosphite, e.g., triphenyl phosphine and an amine base such as pyridine or triethylamine, to obtain a thioester compound of formula III.

The reaction is conducted in an inert, non-hydroxy-containing, organic solvent, e.g., a chlorinated, aliphatic hydrocarbon such as methylene chloride, at a temperature of from −30° to 50° C., preferably −20° to 25° C., more preferably −5° to 5° C. Although the resulting thioester compound of formula III may be isolated and purified by conventional techniques, the crude form of said compound is preferably employed in the following reaction without purification due to the fact that it is rather unstable.

In the second step, a thioester compound produced in Step 1, in purified or, more preferably, crude form, is reacted with the monocyclic amino acid compound of formula IV or the bicyclic amino acid compound of formula V, or an acid addition salt thereof, in the presence of an amine base such as pyridine or triethylamine to obtain a nitrogen-containing mono- or bicyclic compound, respectively. The reaction is conducted in the presence of an inert, organic solvent, e.g., a chlorinated, aliphatic hydrocarbon such as methylene chloride, at a temperature of from −40° to 60° C., preferably −15° to 35° C., more preferably 0° to 25° C., for a period of between 30 minutes and 48 hours. The resultant nitrogen-containing mono- or bicyclic compounds may be purified by conventional techniques, such as recrystallization (if a solid), column chromatography, preparative thin layer chromatography, gas chromatography (if sufficiently volatile), or fractional distillation under high vacuum (if sufficiently volatile).

The α-alkyl amino acids of formula I which are employed in the first step of the instant process are known, having been previously described in U.S. Pat. No. 4,470,972 and U.S. Pat. No. 4,542,234. A particularly preferred α-alkyl amino acid is N-(1-(S)-carboethoxy-3-phenylpropyl)-(S)-alanine.

Similarly, the disulfide compounds of formula II which are reacted with the α-alkyl amino acids of formula I in the first step of the instant process are also known compounds, having been previously described in European Pat. No. 37,380. A particularly preferred disulfide compound is one having the formula

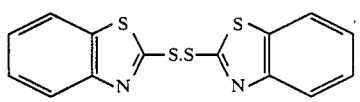

The thioester compounds of formula III which are prepared in the first step of the instant process are novel compounds and, as such, also form a part of the instant invention.

The monocyclic amino acid compounds of formula IV which are reacted with the novel thioester compounds of formula III to prepare the pharmacologically active, nitrogen-containing, monocyclic compounds are known, having been previously described in European Pat. No. 12,401.

The bicyclic amino acid compounds of formula V which are reacted with the novel thioester compounds of formula III to prepare the pharmacologically active nitrogen-containing, bicyclic compounds are also known, having been previously described in U.S. Pat. No. 4,470,972.

The following examples are for the purposes of illustration only and are not intended in any way to limit the scope of the instant invention.

Preparation of a novel intermediate

EXAMPLE 1

N-(1-(S)-carboethoxy-3-phenylpropyl-(S)-alanine-2'-benzothiazolylthioester

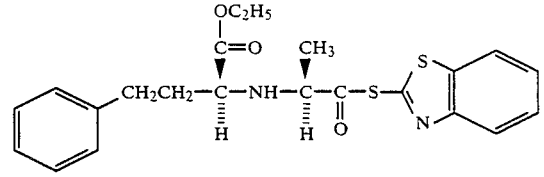

To a reaction vessel was added, with stirring and under a nitrogen atmosphere, 25 g (89.6 mmol) of N-(1-(S)-carboethoxy-3-phenylpropyl-(S)-alanine, 450 ml of dichloromethane and 17.86 g (102.1 mmol) of triethylphosphite. After cooling the mixture to 0° C., 14.9 ml (106.9 mmol) of triethylamine was added, dropwise, while the temperature was maintained at between −3° and 0° C. To the resultant mixture was added, portionwise over a period of 15 minutes, 31.20 g (94 mmol) of bis-(benzothiazol-2-yl)disulfide and this mixture was allowed to react, with continued stirring, for 1 hour while the temperature was maintained at between −3° and 0° C. (Although the reaction mixture may be evaporated to dryness and the resultant residue chromatographed on silica gel using, e.g., a mixture of hexane and ethyl acetate in a ratio of 4:1 as the eluent, to obtain the thioester intermediate as an oil, it is preferred not to isolate the thioester intermediate due to its instability during purification.)

Preparation of pharmaceutically active ACE inhibitors

EXAMPLE 2

7-[N-[1-(S)-Ethoxycarbonyl-3-phenylpropyl-(S)-alanyl]-1,4-dithia-7-azaspiro[4,4]nonane-8-(S)-carboxylic acid

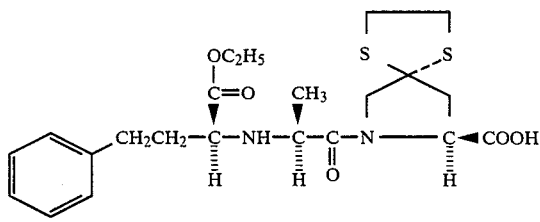

To the reaction mixture of Example 1 containing the unisolated thioester intermediate was added 26.59 g (93.2 mmol) of 1,4-dithia-7-azaspiro[4,4]-nonane-S-carboxylic acid hydrobromide, followed by the dropwise addition of 25.8 ml (185.5 mmol) of triethylamine, during which time the temperature rose to 7° C. The reaction mixture was then allowed to react for 4 hours with continued stirring, during which time the temperature rose to 24° C. The mixture was then washed with dilute hydrochloric acid solution, while the pH of the solution was maintained at 4. The organic phase was then washed with water, dried and evaporated to dryness under vacuum to yield the title compound as a solid.

EXAMPLE 3

7-[N-[1-(S)-Ethoxycarbonyl-3-phenylpropyl-(S)-alanyl]-1,4-dithia-7-azaspiro[4.4]nonane-8-(S)-carboxylic acid hydrochloride monohydrate

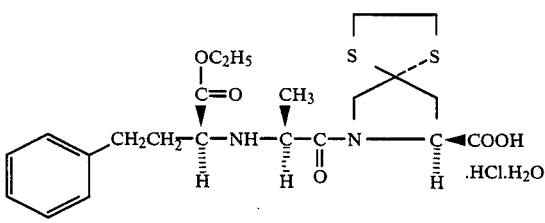

The compound of Example 2 was dissolved in acetone 6.7 ml of concentrated hydrochloric acid was then added, dropwise, and the mixture was stirred at room temperature for 16 hours. The resultant precipitate was then collected on a filter, washed with isopropanol and dried overnight under a high vacuum to yield the title compound as a solid, m.p., 177°–179° C.

EXAMPLE 4

1-[N]-[1-(ethoxycarbonyl)-3-phenyl propyl]-L-analyl]-L-proline

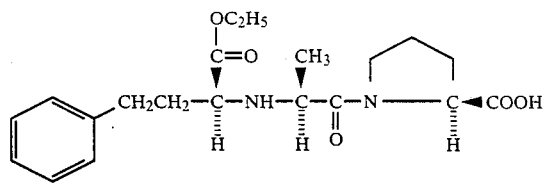

Following essentially the procedure of Example 2, and using in place of the 1,4-dithia-7-azaspiro[4.4]-nonane-8-(S)-carboxylic acid hydrobromide, an equivalent amount of L-proline, the title compound was obtained as a solid.

What is claimed is:

1. A process for preparing a bicyclic compound of the formula:

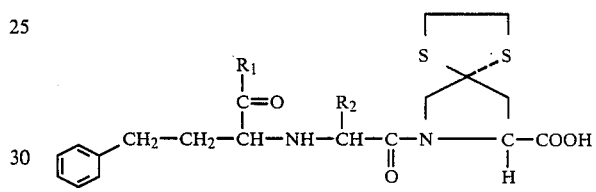

wherein

R₁ is C₁-C₄ alkoxy;

and R₂ is hydrogen or methyl;

which comprises reacting, in a first step, an α-alkyl amino acid of formula I:

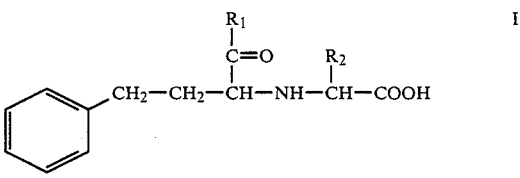

wherein

R₁ and R₂ are as defined above, with a disulfide compound of formula II:

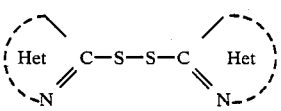

in which the two groups

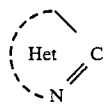

are the same and signify an unsubstituted, 5-membered heterocyclic ring containing one further hetero atom selected from oxygen, nitrogen or sulfur, which heterocyclic ring is fused to an unsubstituted benzene ring, in the conjoint presence of a tri-$(C_1-C_4)$alkyl or a triaryl phosphine or phosphite and an amine base selected from pyridine and triethylamine at a temperature of from $-30°$ to $50°$ C. to obtain a thioester compound of formula III:

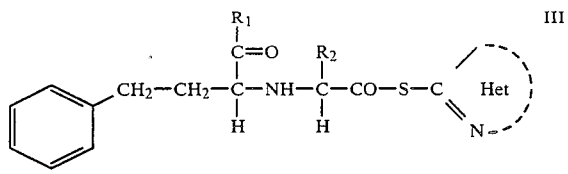

wherein $R_1$, $R_2$ and the group

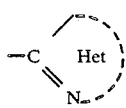

are as defined above,
which thioester compound is then reacted, in a second step, with a bicyclic amino acid compound of formula V:

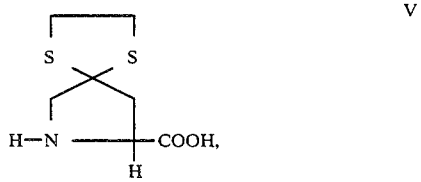

in the presence of an amine base selected from pyridine and triethylamine at a temperature of from $-40°$ to $60°$ C. to obtain said bicyclic compound of the formula

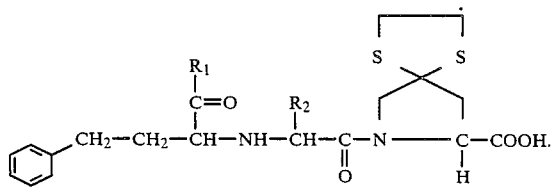

2. A process according to claim 1 wherein the bicyclic compound prepared is one wherein $R_1$ is ethoxy and $R_2$ is methyl.

3. A process according to claim 2 wherein the bicyclic compound prepared is one having the formula

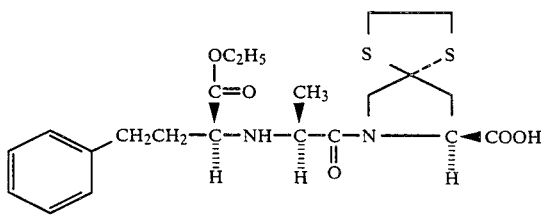

4. A process according to claim 1 wherein the disulfide compound employed in the first step is one having the formula

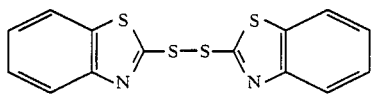

5. A process according to claim 1 wherein the tri-$(C_1-C_4)$alkyl phosphine or phosphite employed in the first step is triethyl phosphite.

6. A process according to claim 1 wherein the triaryl phosphine or phosphite employed in the first step is triphenyl phosphine.

7. A process according to claim 1 wherein the amine base employed in the first step is triethylamine.

8. A process according to claim 1 wherein the first step is conducted at a temperature of from $-20°$ to $25°$ C.

9. A process according to claim 8 wherein the temperature is from $-5°$ to $5°$ C.

10. A process according to claim 1 wherein the the reaction in the first step is conducted in a chlorinated, aliphatic hydrocarbon.

11. A process according to claim 1 wherein the amine base employed in the second step is triethylamine.

12. A process according to claim 1 wherein the second step is conducted at a temperature of from $-15°$ to $35°$ C.

13. A process according to claim 12 wherein the temperature is from $0°$ to $25°$ C.

14. A process according to claim 1 wherein the reaction in the second step is conducted in a chlorinated, aliphatic hydrocarbon.

15. A process according to claim 1 for preparing a bicyclic compound having the formula

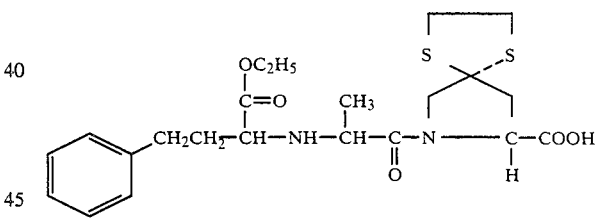

which comprises reacting, in a first step, an α-alkyl amino acid having the formula

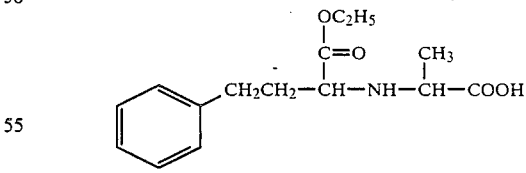

with a disulfide compound having the formula

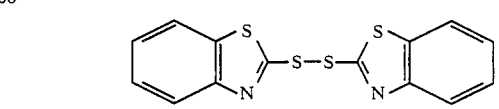

in the conjoint presence of triethylphosphite and triethylamine at a temperature of from $-20°$ to $25°$ C. to obtain a thioester compound having the formula in which the two groups

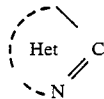

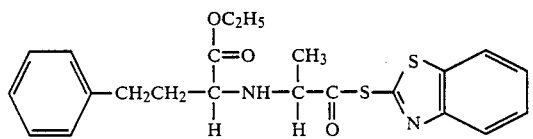

which thioester compound is then reacted, in a second step, with a bicyclic amino acid compound having the formula

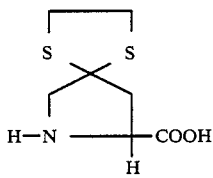

in the presence of triethylamine at a temperature of from −15° to 35° C. to obtain said bicyclic compound of the formula

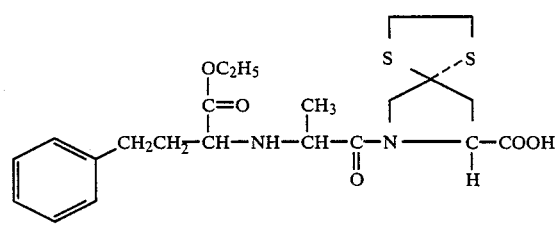

16. A process for preparing a monocyclic compound of the formula:

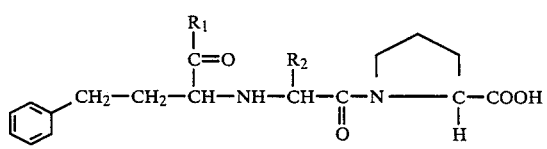

wherein
  $R_1$ is $C_1$–$C_4$alkoxy;
  and $R_2$ is hydrogen or methyl;
which comprises reacting, in a first step, an α-alkyl amino acid of formula I:

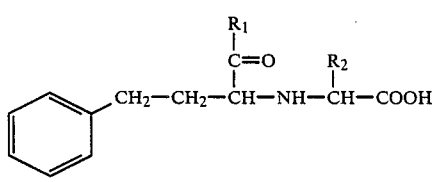

wherein
  $R_1$ and $R_2$ are as defined above, with a disulfide compound of formula II:

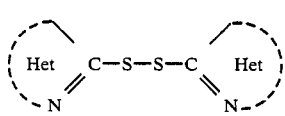

are the same and signify an unsubstituted, 5-membered heterocyclic ring containing one further hetero atom selected from oxygen, nitrogen or sulfur, which heterocyclic ring is fused to an unsubstituted benzene ring, in the conjoint presence of a tri-($C_1$–$C_4$)alkyl or a triaryl phosphine or phosphite and an amine base selected from pyridine and triethylamine at a temperature of from −30° to 50° C. to obtain a thioester compound of formula III:

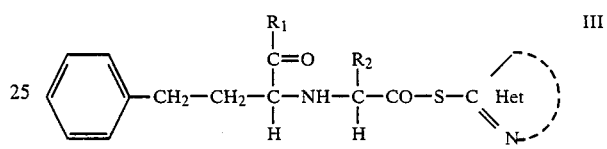

wherein $R_1$, $R_2$ and the group

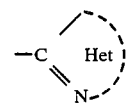

are as defined above, which thioester compound is then reacted, in a second step, with a monocyclic amino acid compound of formula IV:

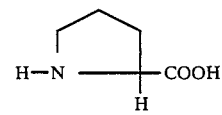

in the presence of an amine base selected from pyridine and triethylamine at a temperature of from −40° to 60° C. to obtain said monocyclic compound of the formula

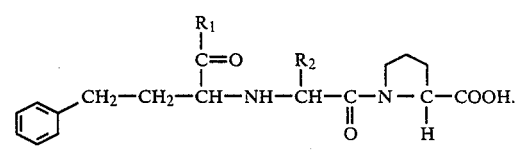

17. A process according to claim 16 wherein the monocyclic compound prepared is one wherein $R_1$ is ethoxy and $R_2$ is methyl.

18. A process according to claim 17 wherein the monocyclic compound prepared is one having the formula

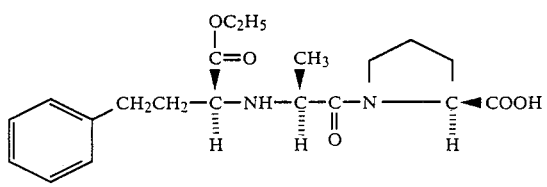

19. A process according to claim 16 wherein the disulfide compound employed in the first step is one having the formula

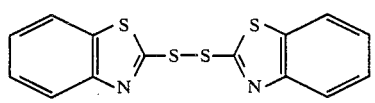

20. A process according to claim 16 for preparing a monocyclic compound having the formula

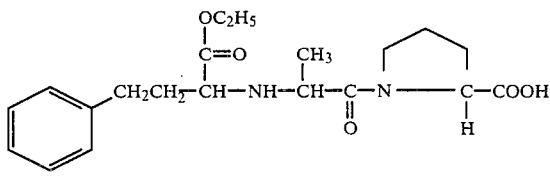

which comprises reacting in a first step, an α-alkyl amino acid having the formula

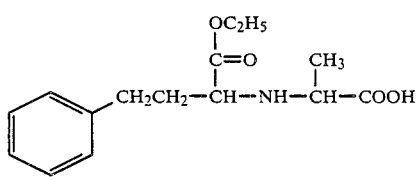

with a disulfide compound having the formula

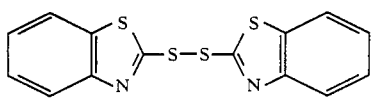

in the conjoint presence of triethylphosphite and triethylamine at a temperature of from −20° to 25° C. to obtain a thioester compound having the formula

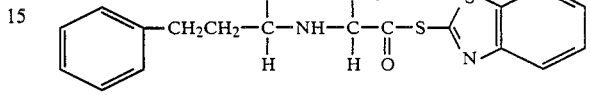

which thioester compound is then reacted, in a second step, with a monocyclic amino acid compound having the formula

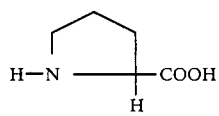

in the presence of triethylamine at a temperature of from −15° to 35° C., to obtain said monocyclic compound of the formula

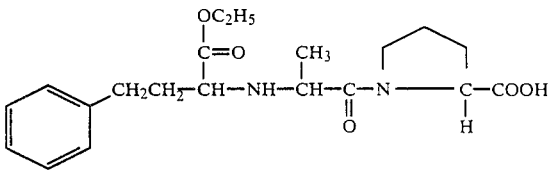

* * * * *